US009965597B2

(12) United States Patent
Becker et al.

(10) Patent No.: US 9,965,597 B2
(45) Date of Patent: May 8, 2018

(54) COLLABORATIVE DRUG DISCOVERY SYSTEM

(71) Applicant: SCHRODINGER, INC., New York, NY (US)

(72) Inventors: Scott Becker, New York, NY (US); Brian Schoolman, New York, NY (US); William C. Jordan, New York, NY (US); Mark Murcko, Holliston, MA (US); Richard C. Friesner, New York, NY (US)

(73) Assignee: Schrödinger, Inc., New York, NY (US)

( * ) Notice: Subject to any disclaimer, the term of this patent is extended or adjusted under 35 U.S.C. 154(b) by 377 days.

(21) Appl. No.: 14/699,824

(22) Filed: Apr. 29, 2015

(65) Prior Publication Data
US 2015/0310006 A1   Oct. 29, 2015

Related U.S. Application Data

(60) Provisional application No. 61/985,685, filed on Apr. 29, 2014.

(51) Int. Cl.
  *G06F 17/00*  (2006.01)
  *G06F 19/00*  (2018.01)
  *G06F 17/30*  (2006.01)

(52) U.S. Cl.
  CPC ...... *G06F 19/709* (2013.01); *G06F 17/30011* (2013.01); *G06F 19/705* (2013.01); *G06F 19/706* (2013.01)

(58) Field of Classification Search
  CPC ............ G06F 19/709; G06F 17/30011; G06F 19/705; G06F 19/706
  (Continued)

(56) References Cited

U.S. PATENT DOCUMENTS 7,146,384 B2 * 12/2006 Sawafta ............ G06F 17/30572
9,535,583 B2 *  1/2017 Smellie ............... G06F 3/04842
(Continued)

OTHER PUBLICATIONS

Brodney, Marian D., et al., "Project-Focused Activity and Knowledge Tracker: A Unified Data Analysis, Collaboration, and Workflow Tool for Medicinal Chemistry Project Teams", J. Chem. Inf. Model., vol. 49, American Chemical Society, © 2009, pp. 2639-2649.*

(Continued)

*Primary Examiner* — Robert Stevens
(74) *Attorney, Agent, or Firm* — Fish & Richardson P.C.

(57) ABSTRACT

Methods and systems for drug discovery collaboration provide collaborative drug discovery electronic workplaces simultaneously accessible by multiple user computing devices. In certain embodiments, a server computer running a server side application communicates with multiple user computing devices. The server side application communicates with electronic databases that define the parameters of each electronic workplace. Each workplace includes an indication of one or more items, such as compounds, and data pertaining to such items, such as computational and experimental data. Updates to a workplace made by one user may be saved to the workplace definition and propagated and displayed to other users. New items of interest may be added to a workplace. A new item added to a workplace may also be saved to the database and registered with the system for use by other users and in connection with other workplaces.

8 Claims, 13 Drawing Sheets

(58) Field of Classification Search
USPC .......................................................... 707/608
See application file for complete search history.

(56) References Cited

U.S. PATENT DOCUMENTS

| | | | | |
|---|---|---|---|---|
| 2002/0029255 | A1* | 3/2002 | Glynias | G06F 17/30557 709/218 |
| 2002/0154172 | A1* | 10/2002 | Linsey | G06F 3/00 345/804 |
| 2002/0194201 | A1 | 12/2002 | Wilbanks et al. | |
| 2004/0003000 | A1* | 1/2004 | Smith | G06F 19/702 |
| 2004/0153509 | A1* | 8/2004 | Alcorn | G06F 3/00 345/804 |
| 2004/0265909 | A1 | 12/2004 | Blaney et al. | |
| 2005/0289166 | A1 | 12/2005 | Stanley et al. | |
| 2007/0043694 | A1* | 2/2007 | Sawafta | G06F 17/30572 |
| 2008/0016116 | A1* | 1/2008 | Tarr | G06F 19/324 |
| 2012/0023418 | A1* | 1/2012 | Frields | G06Q 10/101 715/756 |
| 2012/0110087 | A1* | 5/2012 | Culver | G06F 17/5004 709/205 |
| 2012/0259847 | A1* | 10/2012 | Gierlack, II | G06F 17/30575 707/732 |
| 2013/0275413 | A1* | 10/2013 | Snir | G06F 17/30554 707/722 |
| 2014/0039921 | A1* | 2/2014 | Broverman | G06F 17/30011 705/2 |
| 2014/0101571 | A1* | 4/2014 | Lewis | H04L 65/403 715/753 |
| 2014/0282106 | A1* | 9/2014 | Smith | G06F 17/30165 715/753 |

OTHER PUBLICATIONS

Williams, Antony J., et al., "Mobile apps for chemistry in the world of drug discovery", Drug Discovery Today, vol. 16, Nos. 21/22, Elsevier, Nov. 2011, pp. 928-939.*

Waller, Chris L., et al., "Strategies to support drug discovery through integration of systems and data", Drug Discovery Today, vol. 12, Nos. 15/16, Elsevier, Aug. 2007, pp. 634-639.*

Klein, Karsten, et al., "Scaffold Hunter: Facilitating Drug Discovery by Visual Analysis of Chemical Space", VISIGRAPH 2012, Rome, Italy, Feb. 24-26, 2012, pp. 176-192.*

Harrow, Ian, et al., "Towards Virtual Knowledge Broker services for semantic integration of life science literature and data sources", Drug Discovery Today, vol. 18, Nos. 9/10, Elsevier, May 2013, pp. 428-434.*

Baede, Eric J., et al., "Integrated Project Views: Decision Support Platform for Drug Discovery Project Teams", vol. 52, American Chemical Society, © 2012, pp. 1438-1449.*

Sun, Huarong, et al., "ChemDataBase—A Database Management System for Facilitating Data Management in Computational Chemistry", 2008 International Multi-symposiums on Computer and Computational Systems, IEEE Computer Society, © 2008, pp. 190-193.*

Lee, Man-Ling, et al., "DEGAS: Sharing and Tracking Target Compound Ideas with External Collaborators", J. Chem. Inf. Model., vol. 52, American Chemical Society, © 2011, pp. 278-284.*

Ekins, Sean, et al., "Open Drug Discovery Teams: A Chemistry Mobile App for Collaboration", Molecular Informatics, vol. 31, © 2012 Wiley-VCH Verlag GmbH & Co. KGaA, Weinheim, Germany, pp. 585-597.*

PCT International Search Report and Written Opinion from PCT/US15/28309 dated Aug. 4, 2015, 9 pages.

* cited by examiner

COLLABORATIVE DRUG DISCOVERY SYSTEM

CROSS REFERENCE TO RELATED APPLICATION

This application claims the benefit of U.S. Provisional Application Ser. No. 61/985,685, filed Apr. 29, 2014, which application is incorporated herein by reference in its entirety.

BACKGROUND

Field of the Invention

This application relates generally to computer systems and methods for collaborative drug discovery.

Description of Related Art

In recent years, more powerful computers with vastly improved computing speed and memory storage capacity, together with more mature and accurate computational modeling and simulation techniques and algorithms, have made it possible to solve complex problems in the areas of chemistry, biology, materials science, and other scientific disciplines. Computational software packages are currently available to study and compute properties of a wide variety of molecules/compounds. Some of these software packages have found applications in computer aided drug design (CADD), which aims to speed drug discovery research by making accurate predictions about the interactions between a drug of interest and its target protein.

The overall drug design process often requires deep and frequent interactions between computational chemists and medicinal chemists for multiple reasons, such as: to generate ideas for new molecules to be synthesized, to make predictions about the properties of molecules under consideration for synthesis, and to discuss the results of simulations and experiments. These interactions have been traditionally accomplished via sharing a whiteboard, passing around pieces of paper with ideas or notes scribbled on them, or using a standalone desktop software application and looking at each other's computers or passing around static and independent files. Such interactions are especially difficult when the participants in the discussions are in separate locations.

While the numerous modern office productivity tools and computational tools can expedite the process of drug design and development, the use of these tools by a large group is riddled with inefficiencies. For example, the commonly used software tools (e.g., spreadsheets, database, SAR/cheminformatics, enumeration tools, modeling, literature/patent search tools, etc.) are often disconnected and incompatible, forcing users to spend time migrating data between applications and ultimately limiting the usage of these valuable assets. Creating, filtering, and organizing large sets of personal notes, proposals, or other documents/files can be particularly challenging. Worthwhile ideas in drug design may take a long time to capture by an individual, but can get lost in brainstorming sessions or over time. Collecting and reviewing ideas from a collaborative team can be time consuming. Duplicate (and potentially wasteful) efforts by the team members may also occur. All of these problems are exacerbated when participants are not physically co-located.

The currently available collaborative computing applications often require that cooperating client computing environments have pre-loaded one or more client-side collaborative computing applications for performing a content sharing and/or collaboration session. Some currently available web-based tools in online collaboration can allow multiple users to view and make changes on remotely stored documents simultaneously and the changes can be reflected in other users' browsers in real time. Representative examples of such systems include Google Docs and Microsoft Office Web Apps. However, such tools are typically limited to sharing and collaborating on relatively simple documents, such as text, spreadsheet, and objects (e.g., charts, comments) embedded within such documents.

Thus, there is a need for a system and integrated platform that provides a centrally managed application with intuitive and convenient interface and tools to allow easy collaboration among members of a drug discovery team, for example, to easily capture chemical ideas and comments about those ideas, and to improve the productivity of online collaborations.

SUMMARY

Certain embodiments of collaborative drug discovery systems and methods include a server side application communicating with user computing devices running, for example, a web browser. Users are provided a graphical interface for creating collaborative electronic dynamic spreadsheet, document or other workplace, referred to in the present embodiments as a Live Report. Multiple users may be viewing and working in a Live Report simultaneously. The contents of a Live Report are reflected in one or more electronic databases accessible by the server side application. User may create or import an item (e.g., compound) for evaluation as part of one or more Live Reports. Such item may be saved to the system (e.g., in the databases) and thus "registered" with the system for future use and evaluation. The databases may also store any number of data pertaining to the items, as well as calculations and operations that may be performed on or with reference to such items. For example, where the items of interest are compounds, the database may store computational values that have been determined for certain compounds, as well as formulas for calculating computational values, which is used for compounds added to the system in the future.

BRIEF DESCRIPTION OF THE DRAWINGS

Representative embodiments are shown and described with reference to the accompanying figures, in which.

DESCRIPTION OF CERTAIN EMBODIMENTS OF THE INVENTION

While the disclosed subject matter may be embodied in many different forms, reference will now be made in detail to specific illustrative embodiments, examples of which are illustrated in the accompanying drawings. This description is an explanation of the principles of the disclosed subject matter and is not intended to limit the invention to the particular embodiments illustrated.

According to some embodiments, systems and methods are provided to enable collaborative design efforts in handling complex tasks in chemical, biological, and other arenas. The system includes a web-based platform that permits a collaborative team with members playing different roles, such as a team composed of medicinal chemists and computational chemists, business executives, contract research organizations, partner organizations, in- and out-licensing professionals, patent attorneys, and other "team members," to concurrently or separately access centrally managed "electronic workbooks," carry out database queries, visualize compounds, and share results in real time via client web software application on individual user computing devices. The system provides an intuitive user experience for exploring and managing ideas alongside other project data, and can streamline the workflow of team members in their brainstorming sessions or other online discussions, project review sessions, and other forms of meetings, and make the results and process easily accessible and trackable (e.g., creating a record in multiple fields within the database(s) memorializing which user performed which actions on a Live Report or the system and tracking the status of items of interest, such as compounds, by reflecting which are ready for review by other members of a collaboration team, which compounds have been ruled out and should not be used in connection with certain discovery efforts). In addition, the platform integrates various computational and experimental resources including computational tools, computational models, visualization tools, search/filtering tools, experimental data databases, etc., to improve the effectiveness and enhance the productivity of online collaboration sessions.

While embodiments of the collaborative platform of the present invention are illustrated herein using the design/exploration of chemical compounds as examples, the platform can be used for other design or analytic fields as well, which include but are not limited to areas, such as biologics, materials science, and ligand and structure based design applications.

Figure 1:
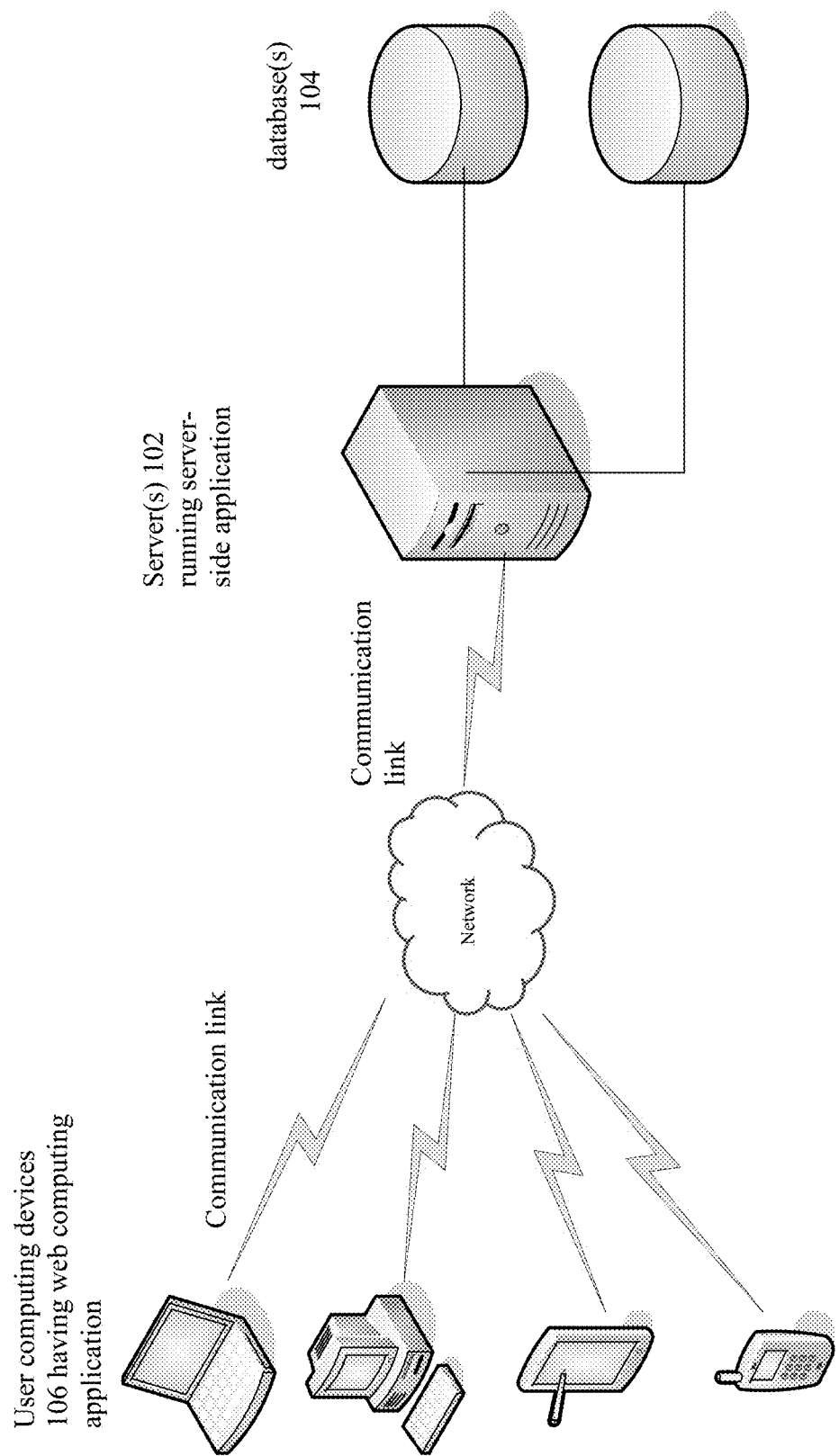
FIG. 1 is a schematic showing a system according to one embodiment of the present invention.

FIG. 1 schematically illustrates a general architecture of a system according to one embodiment of the present invention. The system includes a server side computing application hosted on one or more servers (e.g., web servers) 102 and one or more electronic databases 104 coupled thereto. The server side computing application responds to requests made by a user of a client side network-based interface, e.g., on a web browser installed on a user computing device 106, and delivers the requested contents to the user computing device 106. The server 102 and the user computing devices 106 are connected by communication links such as wired, wireless, or mobile data connections (e.g., LAN, WAN, Internet). Such communication may be established, for example, via a TCP connection using the WebSocket protocol. The server side computing application supports collaboration sessions participated in by multiple users, where changes made on a shared resource in the collaboration by one user are delivered to other users according to predetermined system configurations as well as each user's preferences or settings.

It should be understood that embodiments of the present invention may be applied to different architectures. For example, in an alternate embodiment, the user computing devices are on a separate network, such as a LAN or WAN, that includes a user server and proprietary electronic database (such as described below). Such user networked system is in communication with the servers providing the server side application and the other databases via, for example, the Internet or other network.

The server side computing application can include different modules (or "engines") implemented in computer programming/software running on one or more processors of the server(s) 102 to handle different tasks, including those requested by the user from the web-based user interface. For example, the server side computing application can include database access modules or functions to retrieve data from the databases 104 that satisfy users' queries or that are needed to perform functions described herein. It is to be understood that the database(s) 104 may be supplied by the provider of the system or may be proprietary to one or more users, e.g., connected to the system via an API. Such an API is utilized when executing dynamic database queries to access a user's proprietary database that may or may not be in a different format than the databases of the system and the database fields. The API essentially maps the contents of such proprietary database to the corresponding queries and fields known to the server side application.

Additionally, the server side application can provide access to collaborative data, store the collaborative data, and deliver the data to the user browsers, and store the data in a server memory or databases 104. The server side computing application can include program code written in any suitable server side programming language, such as scripting languages (e.g., Python, Ruby, PHP), Java, Microsoft .Net, etc., and can interface with other code or be extended to execute scripted tasks. It can also include tools or APIs to interface with other software hosted on the same or different servers. In general, the server side application delivers the requested contents to the user computing devices in the form of webpages coded in HTML and/or XML. Although only one server 102 is depicted in FIG. 1, a cluster of servers or server cloud can be used, and the server-side application can be configured and distributed on one or multiple servers to carry out any tasks via distributed or parallel computing. Further, different computational modules for computer simulations can reside on different servers, taking advantage of the hardware and software available on each server.

The client computing environment can generally include a web computing application installed on the user (client side) computing device 106. As used herein, a user computing device 106 can be a desktop computer, a laptop computer, a mobile device such as a smart phone (e.g., one based on Android, iOS, Windows Mobile, etc.), a PDA, a tablet (e.g., Nexus 10, Nexus 7, iPad, GalaxyTab, Amazon Kindle HDX), as well as other smart devices such as Google Glass, Oculus Rift, smart wristwatches, etc. The web application can be a generic web browser, such as Microsoft Internet Explorer®, Mozilla® Firefox, Chrome®, Safari®, etc. (including their desktop versions as well as mobile versions for mobile operating systems such as iOS® and Android®), or another web-enabled application which can interpret and display webpages encoded in HTML or similar technologies as well as interpret/execute instructions contained in the webpages (e.g., Javascript, Java, etc.). The web computing application can maintain certain configuration parameters (e.g., a web browser supporting the operation of Javascript, JAVA applets, DirectX control modules, etc.). As will be appreciated by those skilled in the art, no separate application need be loaded and installed on the user computing device 106 as the server application leverages the generic browser application residing on the user computing device.

In the following, various features and functionalities of the user interface on the client side of the collaborative platform are further described, followed by a description of inner workings of the server side application as well as the information flow between the user computing devices 106, server(s) 102 and databases 104.

Figure 2:
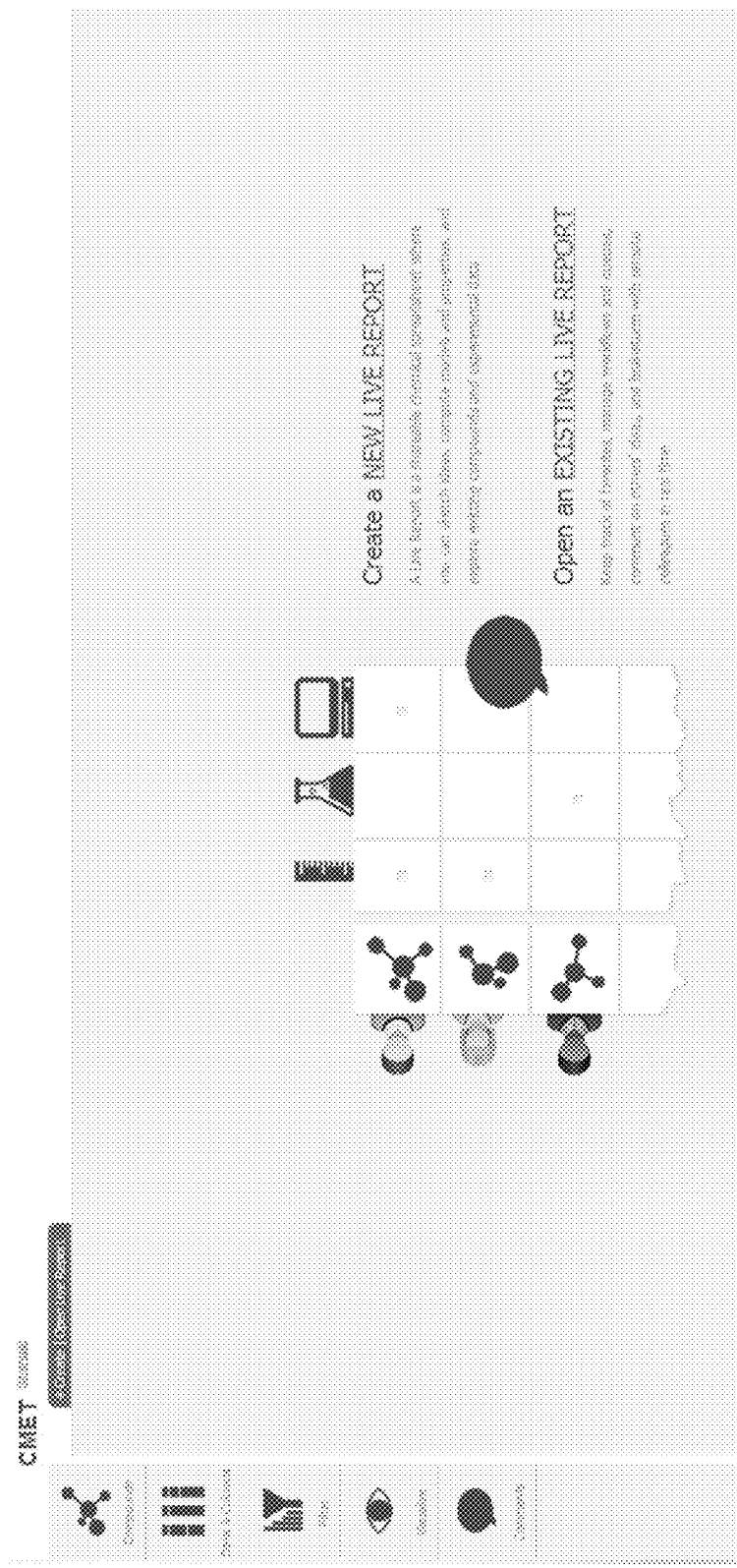
FIGS. 2-4, 5A, 5B, 6A, 6B, 7A, 7B and 8 are illustrative screen shots of a user interface according to embodiments of the present invention.
Figure 3:
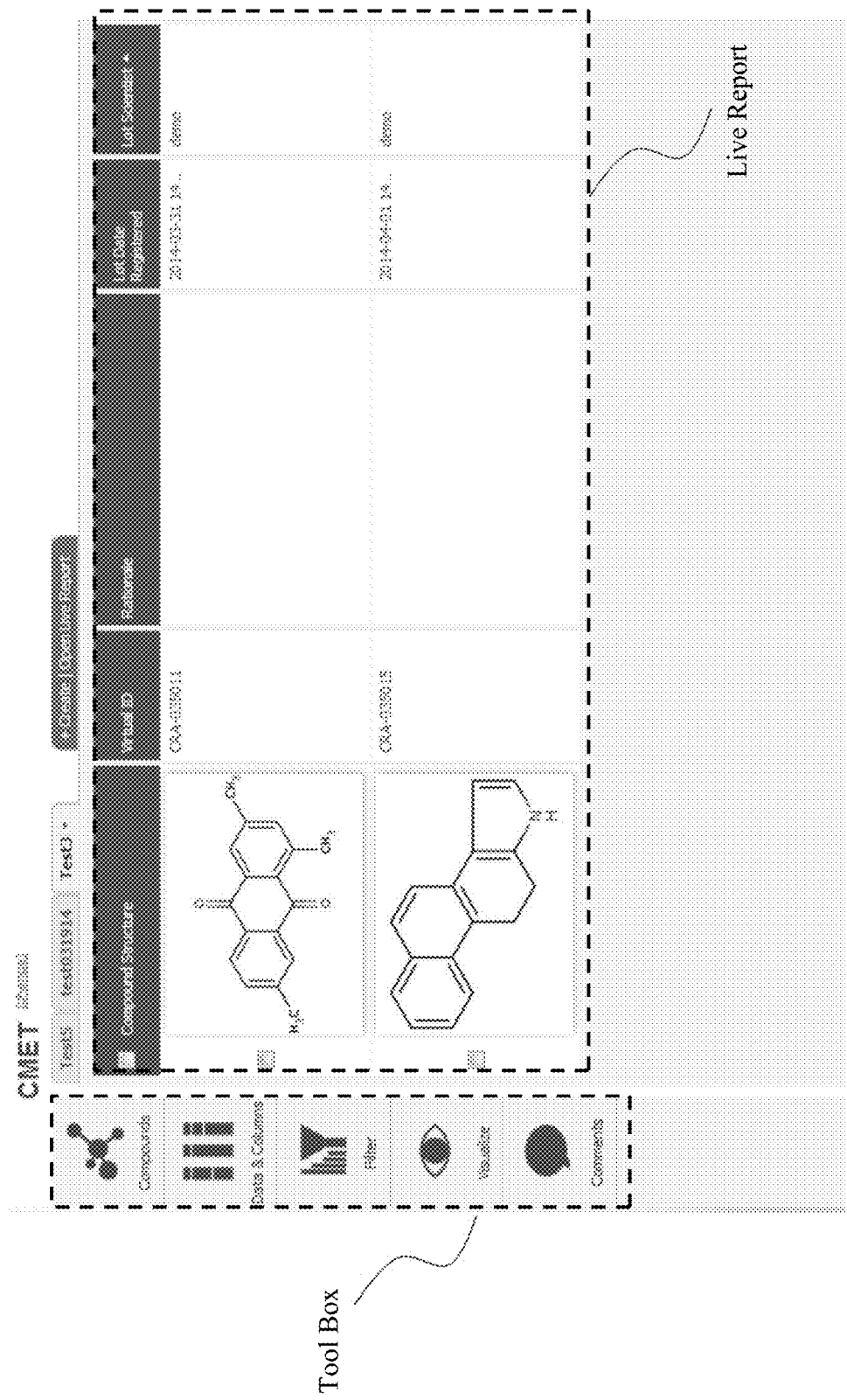
Figure 10:
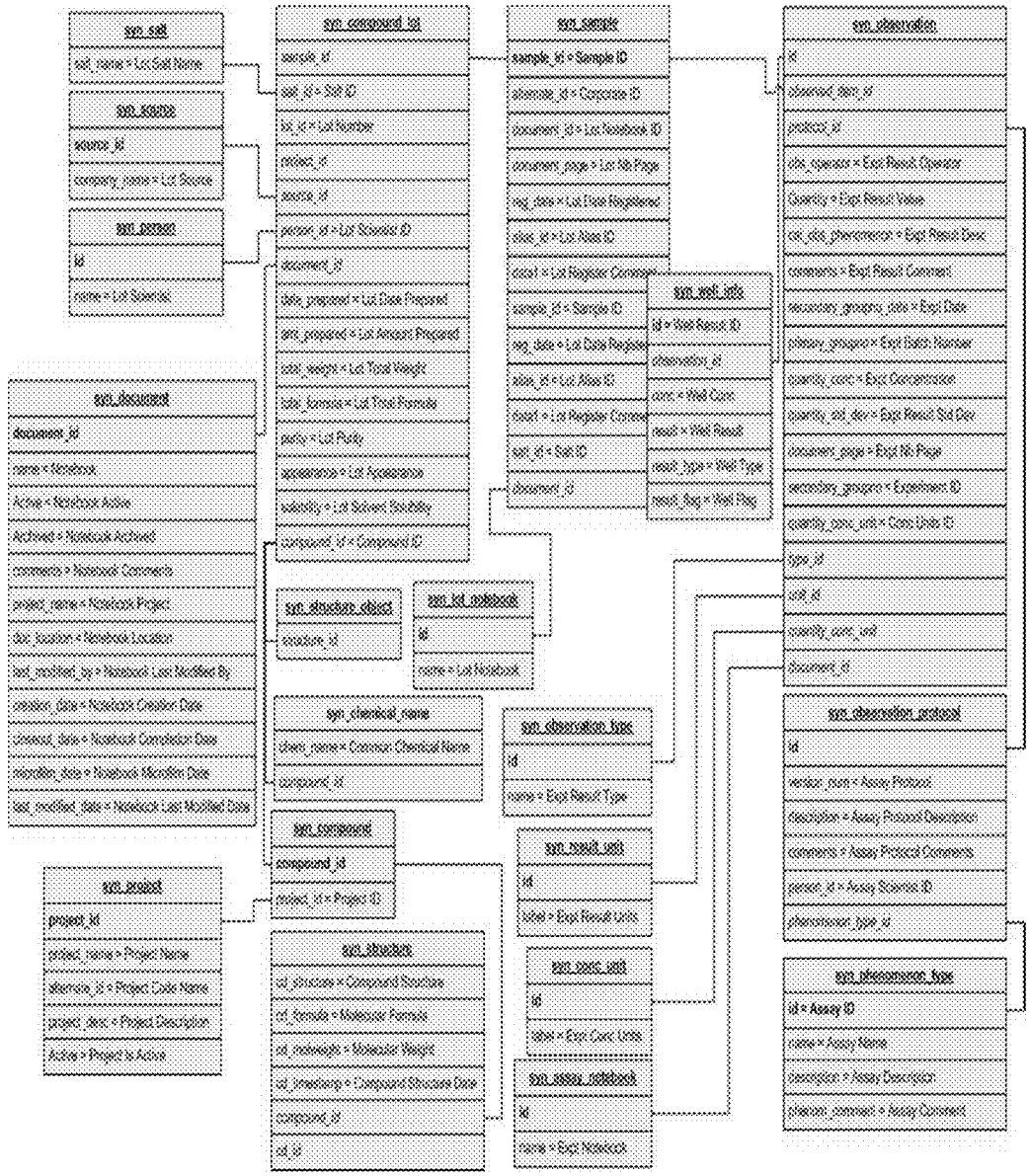
FIG. 10 is a database schema according to one embodiment of the present invention.

To enter a collaborative session, a user can access a website portal which presents a user login page on the user's browser. After entering the login credential and being authenticated by the server 102, the user can be presented with an interface that resembles what is depicted in FIG. 2. The user can be given options of creating a new "Live Report" or opening an existing "Live Report." The term "Live Report" can be considered an illustrative, centrally managed online "workbook" shared by users participating in that Live Report. A Live Report contains a variety of views on data relating to a set of compounds, including but not limited to a grid (or spreadsheet style), plots (such as a scatterplot or radar plot), 3D visualizations, and others. On the server side, a Live Report includes a collection of data retrieved from data tables (for example, as illustrated in the schematic of FIG. 10) in the server-side databases 104 based on a Live Report definition, which is stored as a database query for retrieving data from server side databases that meet the user's specification of the Live Report, e.g., at the client side. When retrieved by the user browser, such data is formatted with page layout commands which can be customized by the user. A default view of a Live Report can be a grid view as illustrated in FIG. 3 and described further below.

If the user selects the option of opening an existing Live Report, the web interface can present the user a list of existing Live Reports that the user is authorized to access (as reflected in the data tables). Upon the user's selection of a Live Report (e.g., by name or ID), the user browser sends a request for the server 102 to load the Live Report definition, retrieve the corresponding data from the server databases (by executing database queries, e.g., to join different tables, as necessary), and transmit such data and formatting information to the user browser. An illustrative retrieved Live Report, with two compound structures in grid view, is shown in FIG. 3. Each row of the grid includes a distinct compound represented by a two-dimensional structure (other representations, such as its chemical name, string representation, as retrieved from the databases, etc., can also be used), a Virtual ID assigned by the system for the compound, the rationale provided for such a compound (e.g., the reason(s) the compound was originally proposed, which can be editable by the creator or other authorized users), Lot Date (which represent the date the compound was first proposed), and Lot Scientist (identifying the name of the person proposing the compound).

Figure 4:
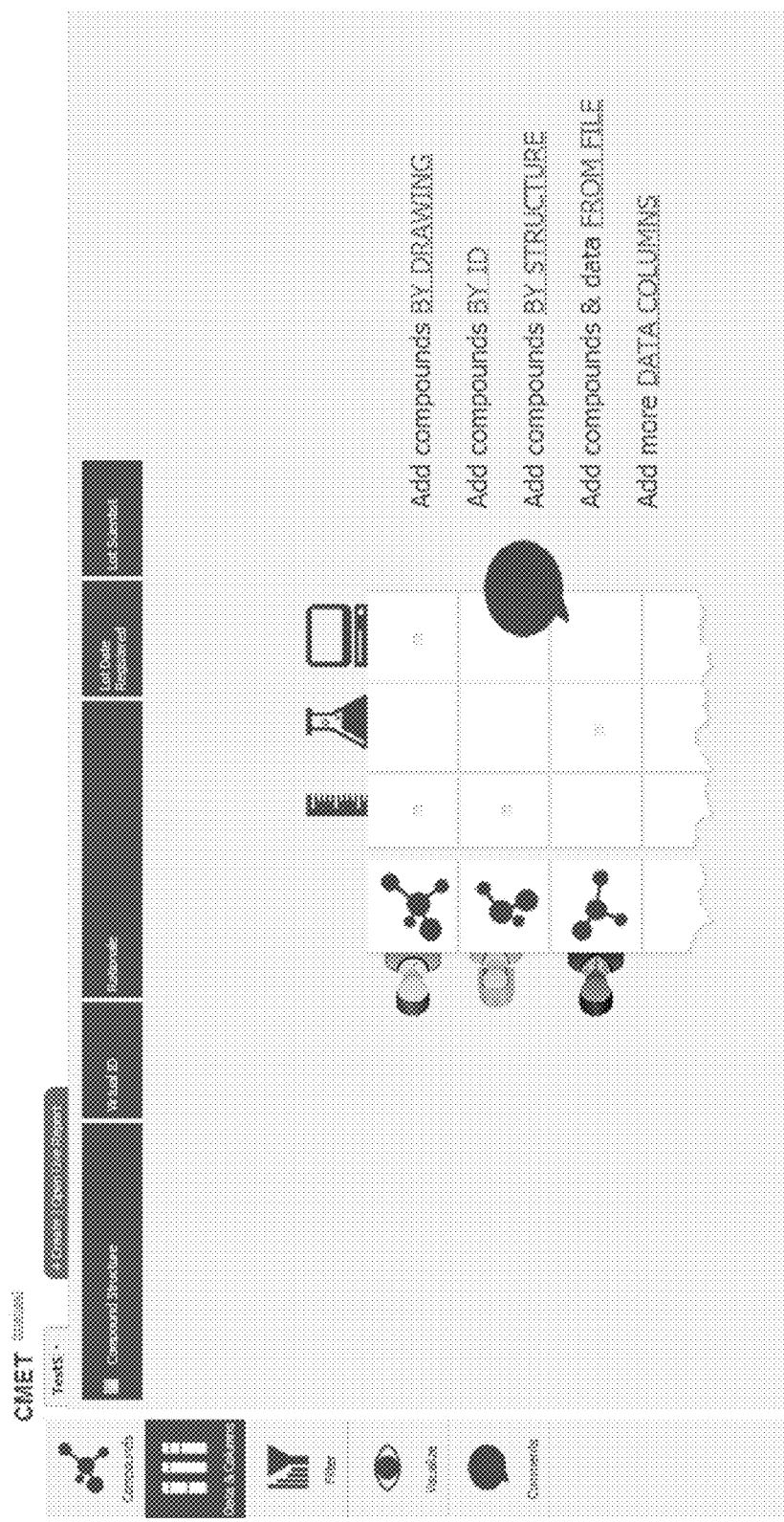

If the user selects the option of creating a Live Report, an interface, such as shown in FIG. 4, can be presented to the user, where the user can add compounds by drawing, ID, structure, or from a data file of preexisting compound(s). The user can also create a new Live Report or open additional Live Reports by using the tab "+Create|Open Live Report" shown on the top of the webpage of FIG. 3 and FIG. 4.

The user can use tools, an illustrative, non-exclusive list of which is shown on the left side of the web interface (the "tool box," labeled in FIG. 3) to manipulate and edit the Live Report. As shown in FIG. 3, the tools in the present embodiment (from top to bottom) include "Compounds," "Data & Columns," "Filter," "Visualize" and "Comments." In other embodiments, additional or different tools may be included. It is to be understood that the tools shown and described herein are merely illustrative and that additional or fewer tools may be included in embodiments. In certain embodiments, the server side application includes APIs that provide a mechanism for users of the application to interact via custom integrations, such as custom tools. In such embodiments, the API provides a means to make calls to the system databases for executing queries and thus retrieving data, as well as adding, deleting and otherwise updating them Furthermore, the presentation of tools, and the user interface in general, may take different forms, for example, with tools be presented elsewhere in the interface (e.g., via submenus).

Figure 5A:
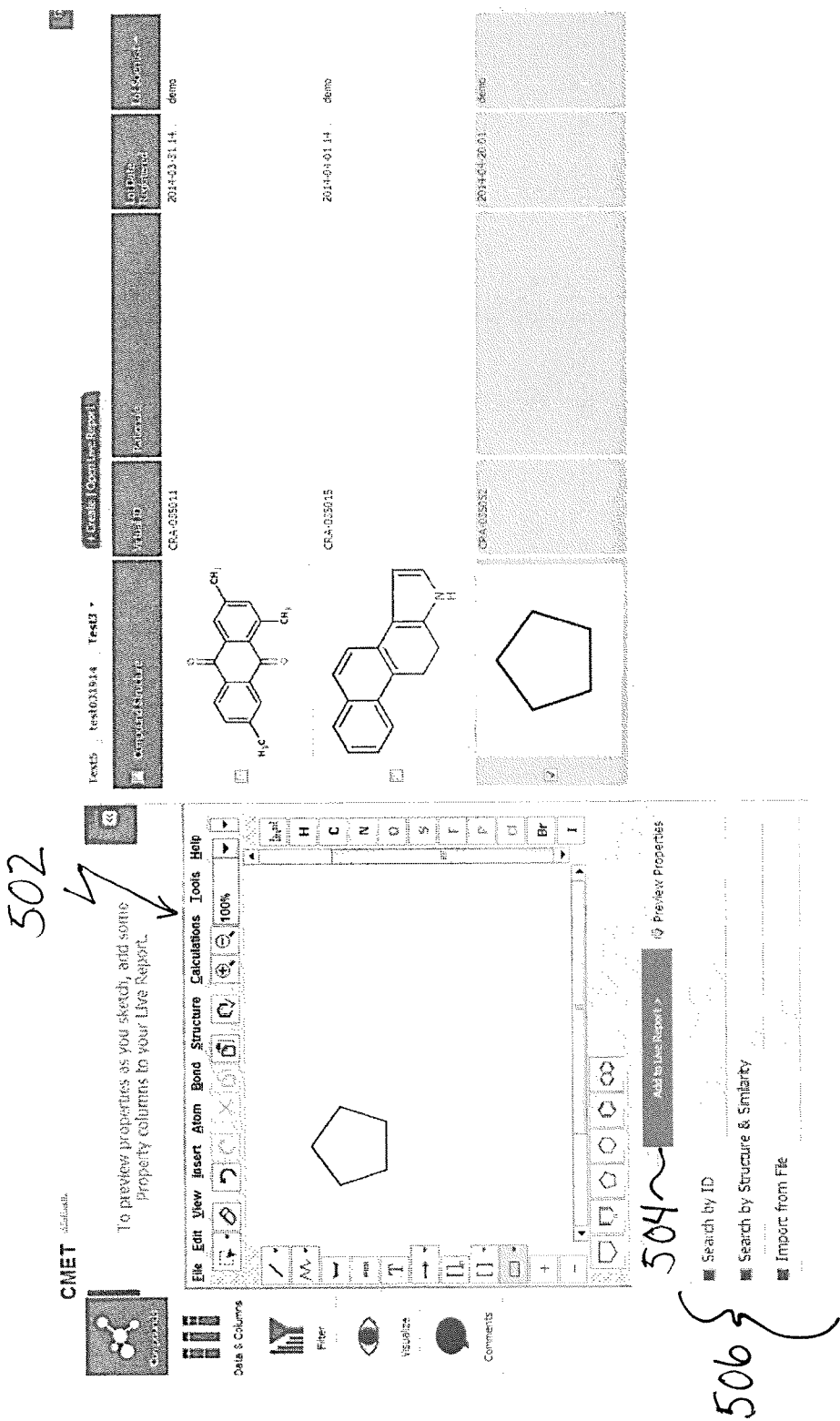

When the "Compounds" tool is selected (here, clicked), a panel area is displayed on the webpage which allows the user to create new compounds for inclusion in the Live Report, or import existing compounds (e.g., those already stored in the server or local databases). For example, a chemical drawing program or sketcher 502 (which may be a downloaded JAVA applet or implemented in a scripting language, such as Javascript, which would not require a scripting language to be installed or an applet to be downloaded) can be displayed, allowing the user to build a compound in the drawing canvas of the program using the graphical tools and other commands provided in the program (see FIG. 5A). Upon completing the chemical structure of the compound, the user can click the "Add to Live Report" button underneath the drawing canvas to add the compound to the grid view (e.g., a cyclopentane is drawn in the drawing program and added to the Live Report, as illustrated in FIG. 5A). Adding a new compound to the Live Report can also trigger an automatic database inquiry to generate the data for the columns in the Live Report corresponding to the new compound (which may also include performing new computational tasks if needed) and providing the data to the user computing device(s) for display as a part of the Live Report. For example, the Live Report may include one or more Properties (discussed below) for compounds (entries) that are updated in real time.

A compound can be also added to the Live Report by other methods, such as by searching by ID or structure (or structural similarity) in the server database, or imported directly from a file (e.g., any supported file format, such as CSV, SDF, and other formats) 506. For example, if the user selects (activates) "Search by Structure & Similarity," a sketcher program can be displayed to the user that allows the user to enter a core structure, and additional buttons that, upon user activation, requests the server to perform a search in the server databases for compounds that contain either the same core structure or have structures similar to the core structure. Alternatively, the web interface can allow the user to generate compounds via scaffold based Markush or reaction based enumeration by selecting a starting core structure, setting the options of substitution groups, and a set of desired fragment libraries.

Figure 5B:
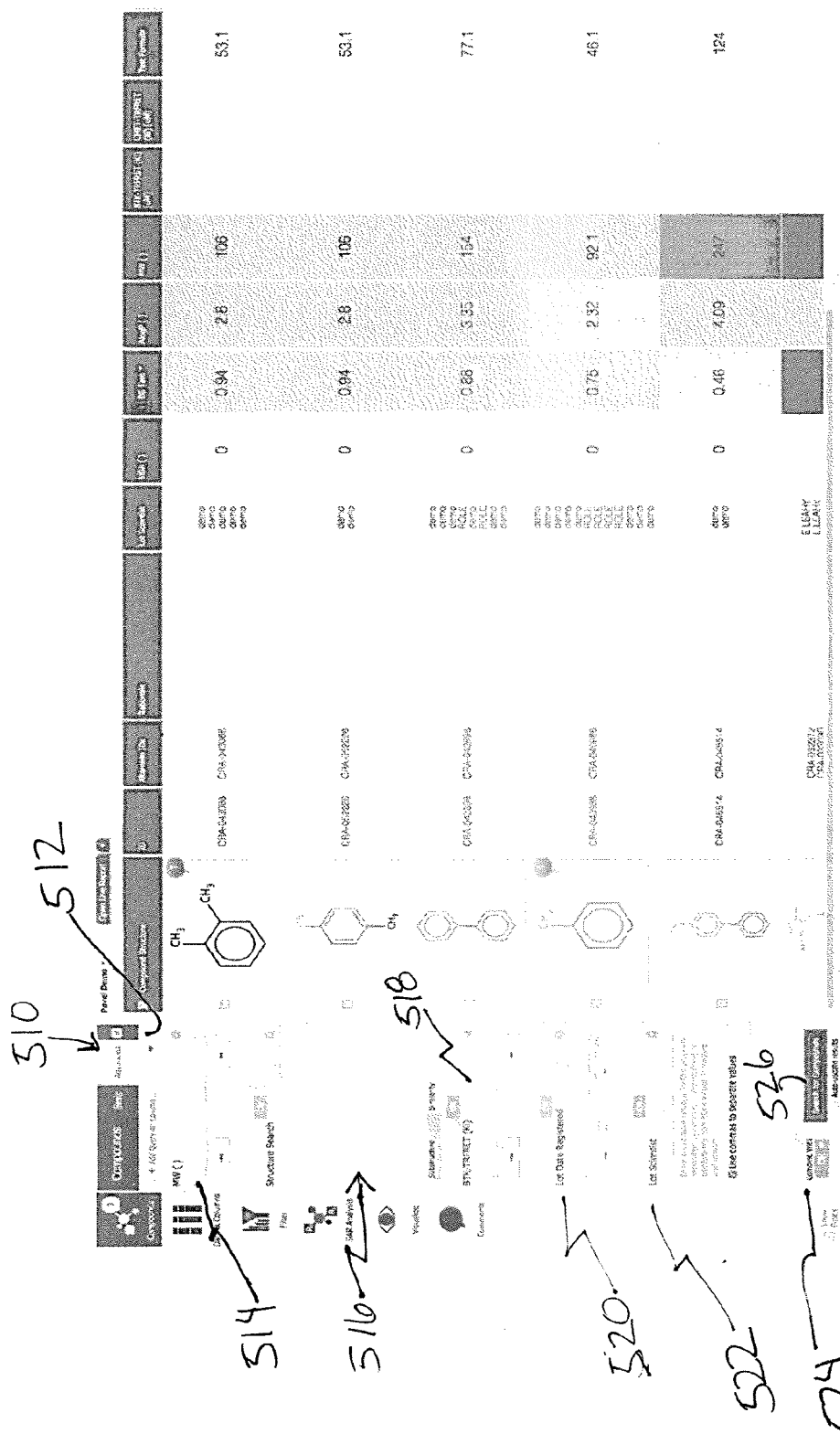

A user may select an option to define a query and associate it with a Live Report. As illustrated in FIGS. 5A and 5B, there are two types of queries that may be performed in response to instructions or inputs from users, which are referred to herein as basic queries and advanced queries. In the present embodiment, basic queries do a one-time search to bring compounds into a Live Report based on structure (exact, substructure, or similarity) or ID. Advanced queries can be one time or persistent (always look for compounds with this criteria as data in the system is updated/added/removed). Advanced queries allow a user to search both based on structure and associated data stored in the databases 104. In the present embodiment, whereas advanced queries actually change the data included in a Live Report, basic queries do not. Queries may be associated with a Live Report (e.g., the search may be to include in the Live Report any new compounds meeting certain criteria (e.g., having a particular R-group) added to the databases since the user's last access to the Live Report (e.g., as reflected in the database)) or may be generated and saved on a system-wide basis and not limited to a specific Live Report.

In one embodiment, a user may select an option to define an advanced query, in which case the sub-window 510 of FIG. 5B, is displayed. In the present embodiment, the user may select a query as previously defined and saved, e.g., via a pull down list 512. A query may involve any simple or Boolean operation and search of the information stored in the databases 104 and may be persistent (i.e., is saved in the databases 104 and may be re-run each time the associated Live Report is executed or generated). The search query itself may be stored in a table and associated in the databases 104 with a specific Live Report or multiple Live Reports, for example, all Live Reports created by a particular user. Thus, as will be appreciated by those skilled in the field, embodiments including both the basic search and the advanced search permit users two levels of search capability—persistent advanced queries and non-persistent, dynamic basic queries—which provides enhanced flexibility and technical efficiency in accessing the data in the electronic databases 104.

As shown in FIG. 5B, a query may include an indication of an acceptable molecular weight (MW) or range of weight 514; a structure search 516, such as having a particular R-group or other substructure or similarity; acceptable BTK-TRFRET (Bruton's tyrosine kinase—time-resolved fluorescence resonance energy transfer) value or range thereof 518; and acceptable lot date or range thereof 520; one or more scientists 522. With regard to a structure search for similarity, it will be appreciated that such searching may be of data related to the structure or any given property of the structures (compounds). The system also permits the user (or administrator) to enter a custom algorithm for scoring similarity. In one embodiment the user may identify one or more properties, relationship(s) among the properties (e.g., mathematical operations; relative weights, etc.) and desired results of such scoring (e.g., greater score is better, lower score is better, acceptable range, acceptable threshold, etc.). Each of the foregoing fields 514-522 may be combined into a single query, with the user defining the Boolean operator 524. The search is run by activating a "search" button 526. Compounds satisfying a query may be persistently added to the Live Report, so that the next time the Live Report is run, such compounds are included along with the corresponding data in each column. The user is also provided the ability to select the option to have the Live Report automatically updated based on new compounds meeting the query 528. When selected, the databases 104 are updated to save the query and an indication that the query is to be run each time the Live Report is run.

For any pre-existing or newly added compound, the user can request the server 102 to compute a property of interest, such as a basic property including, for example, molecular weight and chiral center count, or a more "advanced" property, which may depend on the computational models and/or algorithms chosen (e.g., quantum mechanics calculations, statistical mechanics modeling and/or simulations (e.g., molecular dynamics simulations, Monte Carlo simulations), docking, free energy perturbations, machine learning, homology, or other approaches), which can include e.g., AlogP, solubility, energies, electronic charge distributions, dipoles and higher multipole moments, vibrational frequencies, reactivity or other spectroscopic quantities, surface area, docking scores, etc.

Figure 6A:
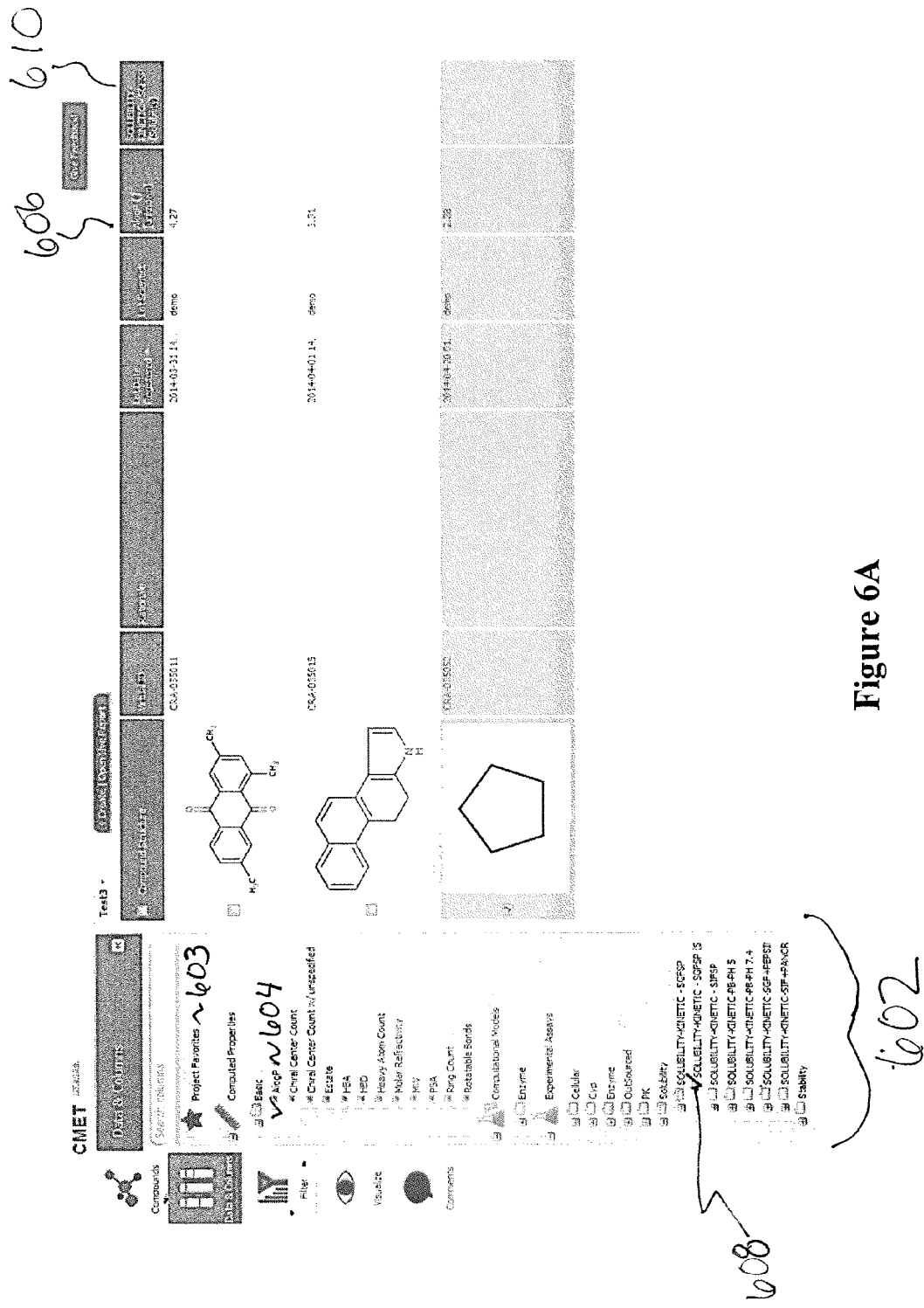

FIG. 6A illustrates a user interface that allows the user to request the server(s) 102 to compute a property of interest for a compound. This function can be accessed by clicking on the "Data & Columns" tool in the tool box, which opens a panel 602 containing a tree menu including various menu items. Illustrative data includes computed properties and computational models, which are calculated by the system, and experimental assays, which are experimental data that has been uploaded into a user's corporate (proprietary) database, which (as explained above) is mapped into the application. Experimental data is data that has come from performing an experiment in a lab, whereas computed properties and computational models reflect computed simulation data. "Project Favorites" 603 denote the ability to mark one or more of the items in the previously noted computed properties, computational models, and experimental assays as a more commonly used data point to be added to Live Reports. If made (identified as) a favorite, the server application causes the computed property, computational model, and experimental assay to be denoted as such (e.g., by setting a flag in the database 104), and it is displayed as such.

Activating (e.g., clicking or double-clicking, as the case may be depending on the defined trigger event) an item in the menu can send a request to the server 102 to compute the corresponding property for all the compounds in the Live Report (or selected compound(s)), and update the Live Report by adding an additional column showing the computation result.

For example, as shown in FIG. 6A, clicking on (or otherwise selecting) "AlogP" 604 in the "Data & Columns" panel results in a request being generated and sent to the server 102 to compute the AlogP property for all the three compounds in the Live Report 606. The server application receives and processes the request by performing the required computation on the data associated with the compound, and sends the computed result back to the browser to be displayed to the user. The computed result is also stored in a table associated with the compound in the database. Such requests can be implemented by AJAX programming techniques, which allows background request and retrieval of data from the server without interfering with the display and behavior of the active webpage. Multiple properties may be added to the Live Report.

The server side application may not need to compute a requested property if such a property has been previously available in a database 104. In handling the request from a user, the server side application can be configured to first check the databases 104 to see if such a property value for a given compound is available in the database (but not included in the current Live Report definition), and if so, simply load the data representing the property value and send it to the user device 106 for display as part of the Live Report (and bypass the computational engine). Thus, clicking on (selecting) a property menu item on the user browser interface can be interpreted as a database query by the server side application, and when it is determined that the value requested is "null," the required computing task will be dispatched by the server side application to the responsible module or engine for performing such a task. As such, processing efficiencies can be achieved, which may be particularly useful in such a collaborative setting. Furthermore, it should be understood that a user's proprietary database, in which proprietary experimental (or other) data not found in the system database 104 (e.g., where the system may be provided by a third party vendor), may be added in communication with the system, and the server side application can be instructed to search such database. This is done via the mapping mechanism noted above, which maps or correlates fields in the proprietary database to fields in the system database(s) 104 (and vice versa). The queries are pre-defined, and a user does not need to understand any database concepts to retrieve data. Databases may be added to the mapping layer (e.g., via an administrator), or in alternate embodiments, are loaded into a highly optimized cache.

While certain of the basic properties of a compound can be computed rather quickly (e.g., as a matter of seconds), some tasks can be computationally demanding in terms of CPU time, memory required, etc. To cope with Live Reports having a large number of compounds and/or requests from users of multiple Live Reports, the server side application may queue the incoming requests (including those requests for performing computational tasks) based on the time or order the requests are made, the estimated completion time of the requests, the urgency or priority of the requests, user priority, Live Report priority, and/or other priority criteria, to meet the users' needs. Such criteria may be saved in the databases (e.g., user and Live Report priorities) or determined as needed. In certain embodiments, when the server 102 receives a computational request, it checks one or more queues of requests, and if other requests are present, it considers the established priority criteria to determine which requests to perform.

The "Data & Columns" tool can also include menu items that allow the user to import experimental data (if available) for a selected compound, e.g., from a server database 104 or a user's local (e.g., proprietary) database. For example, the experimental data for a compound can include biological, pharmacokinetic, and pharmacological assay results, as well as binding affinity of the compound to a given target, drug-likeness, toxicity to target organisms or organs, interactions with target molecules, etc.

As illustrated in FIG. 6A, when a requested experimental data (e.g., Solubility-Kinetic-SGFSP 608) is selected but is not found in the server database, the Live Report grid view can be augmented to include the additional column (e.g., 610), but the cells for the column are blank. Such blank cells can be automatically filled if, at a later time, the experimental data becomes available. Alternatively, when a requested experimental data is unavailable, the Live Report definition remains unchanged (i.e., no new column for the requested experimental data is added), but the user can be notified by an alter message, generated by the server application once the data becomes available. While it is preferred that all experimental data are retrieved by the server from a database and remain not editable by the user of the Live Report (to ensure the validity/integrity of the data), it is also possible to allow the user to directly enter such experimental data, which may be stored in the database and associated with the compound and Live Report. Such directly entered experimental data can be annotated by the user, e.g., by using the comment tool as described herein.

Figure 6B:
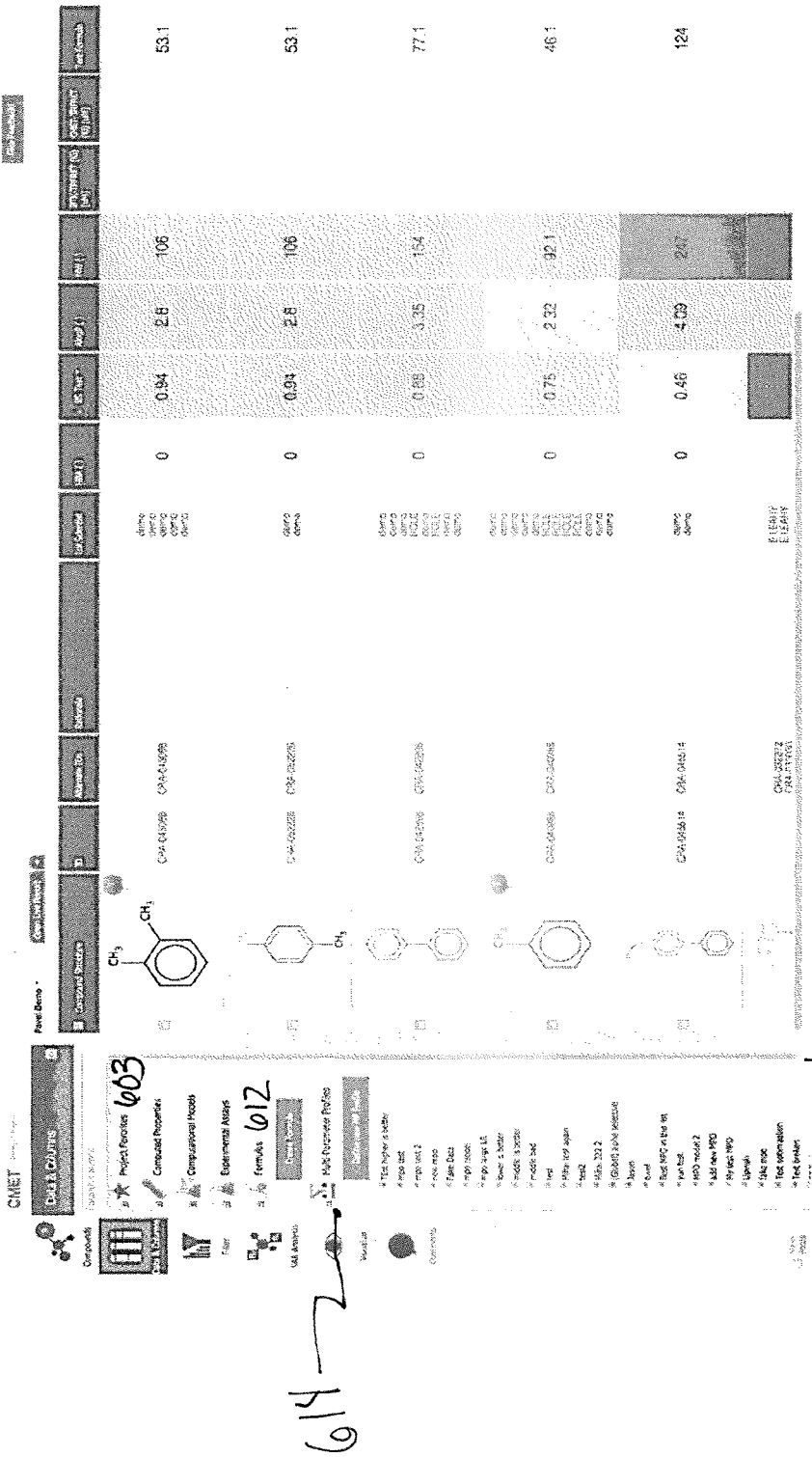

As shown in the alternate embodiment of FIG. 6B, the Data & Columns panel may also include the ability to associate one or more Formulas 612 with the Live Report. The Formulas may be predefined (e.g., defined by the system, an administrator or previously saved to the database by a user for future use in other Live Reports) or user definable based on a menu of selectable operations. The formulas (and an indication of each formula may be saved to the database and associated with the Live Report.

As also shown in FIG. 6B, the Data & Column tab may further include the ability to generate a multi-parameter score for the compounds in the Live Report (indicated as Multi-Parameter Profiles) 614. In general, a Multi-Parameter Profile 612 may provide a score (e.g., absolute or relative) based on multiple computed or experimental values. For example, a Multi-Parameter Profile may rank compounds based on a particular weighting or ratio of each of molecular weight and AlogP value. Additionally, users (which may be administrators) may define visual indicators for the Mulit-Parameter Profile values. For example, the system may automatically filter the compounds and provide a visual indication (e.g., color-coding, shading, etc.) to distinguish those compounds having the desirable value from those that do not. To illustrate, similar to as shown in FIG. 6B, where a higher Multi-Parameter Profile value is desirable, the system may color the top quartile (or some other percent or number) green, the middle quartile (or some other percent or number) yellow, and the remainder (i.e., the most undesirable) red. Multi-Parameter Profiles may be named and saved to the databases 104, and thus be readily available for re-use in other Live Reports.

Figure 7A:
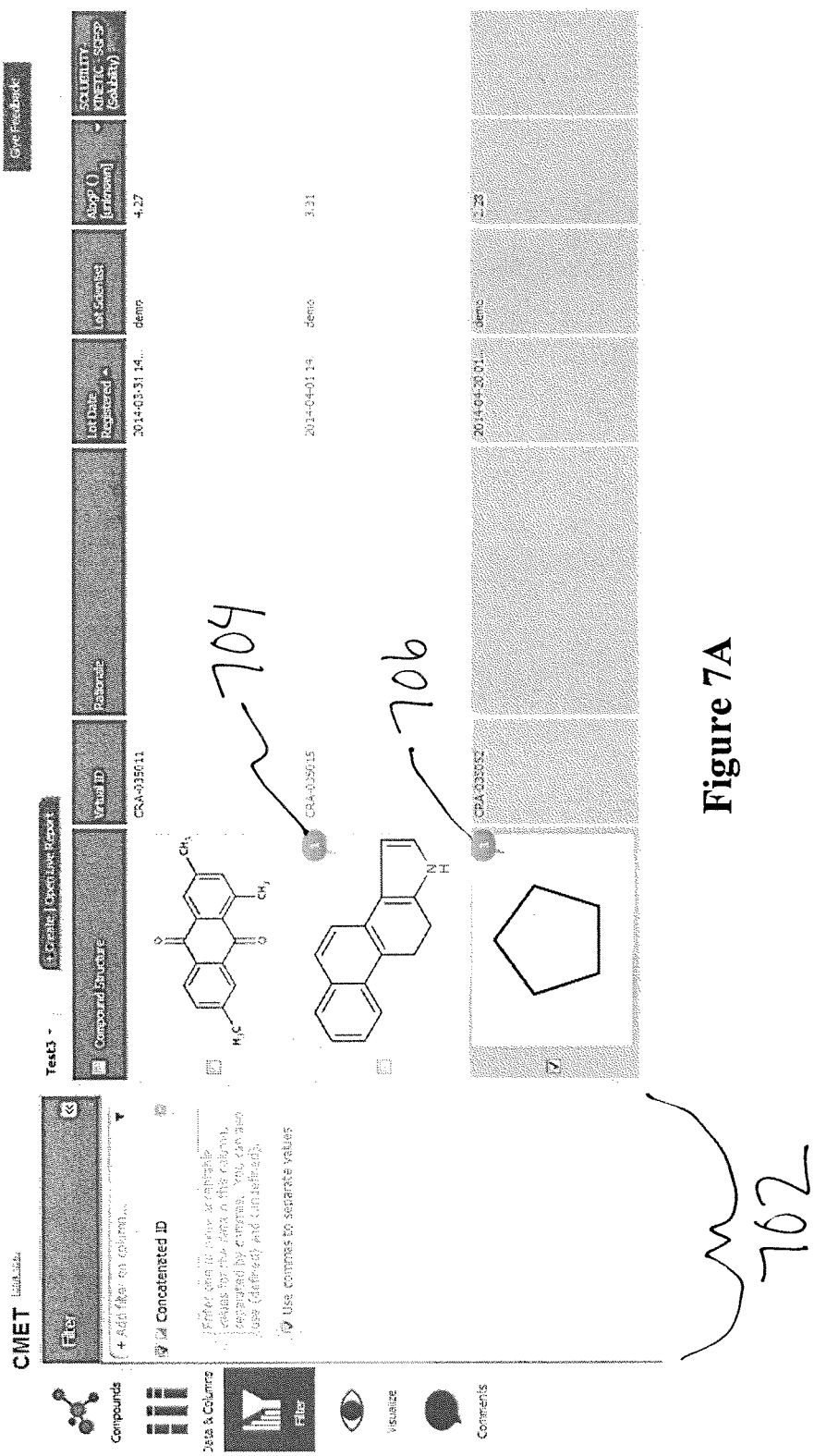
Figure 7B:
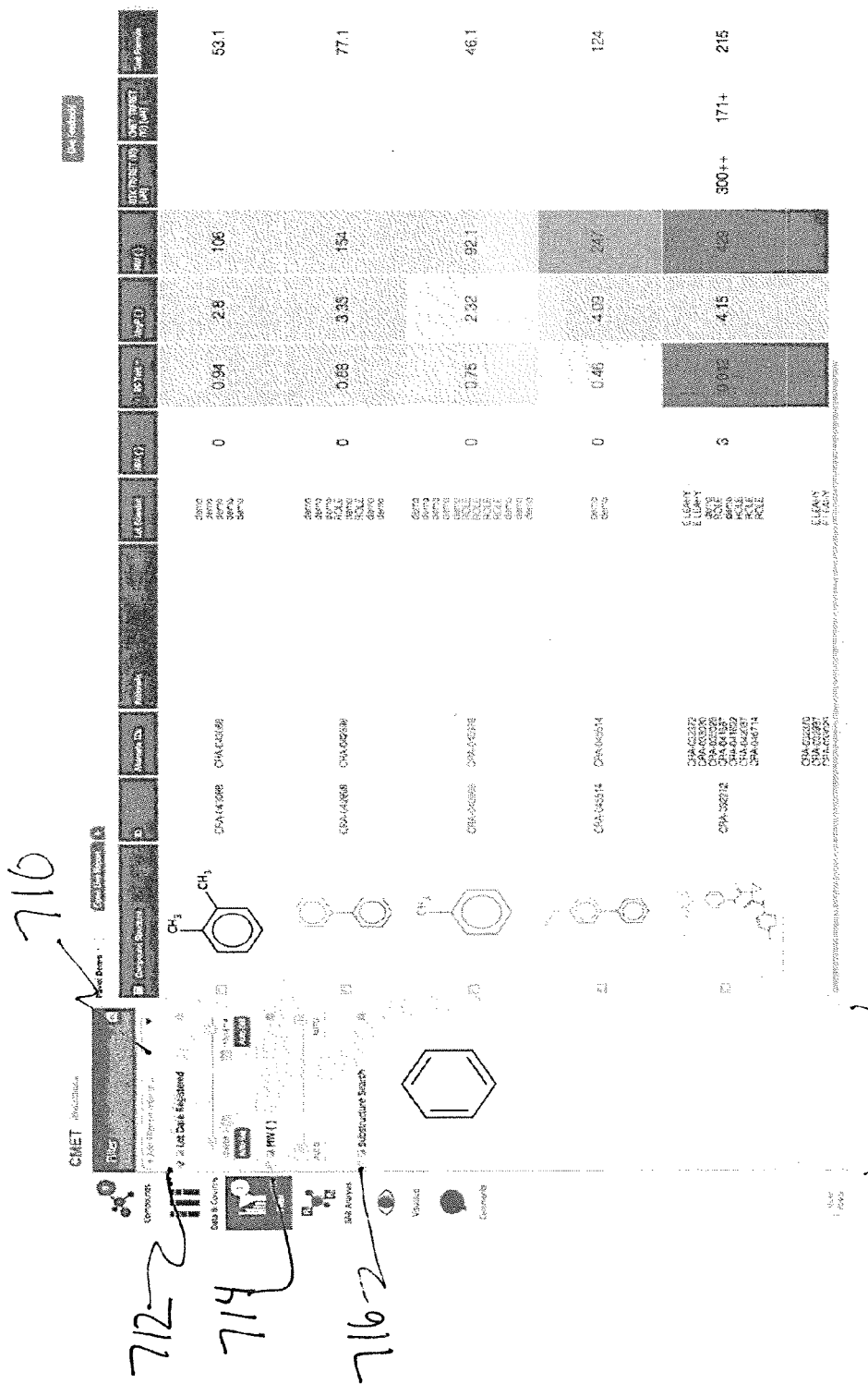

The "Filter" tool of the web user interface can be activated to show a Filter Panel area 702, as shown in FIGS. 7A and 7B (an alternate embodiment), which allows the user to specify a filter or search for data in any one or more columns currently in the Live Report. The server application searches the data for such column(s) in the Live Report, flagging table entries for those rows having compounds data that satisfies the filter value. When a filter is applied for a selected column, only those rows (compounds) that contain data in the specified column that satisfy the provided filter criteria will be shown to the user. In an alternate embodiment, the rows (compounds) not satisfying the filter criteria are still shown, but visually identified as such (e.g., grayed-out). This tool only affects how the Live Report is displayed to users, but does not affect the underlying data of the Live Report (i.e., compounds whose data do not satisfy the filter remain associated with the Live Report in the databases 104). The filter can be included as part of the Live Report definition, in which case, any filter applied by one user will be propagated to the web interfaces of other users by the refresh mechanism discussed herein. An illustrative Filter application is shown in FIG. 7B, in which filtering may be performed based on: any saved filters by virtue of pull-down menu 710; lot date registered (e.g., date range) 712; molecular weight (MW) (e.g., range) 714; and/or substructure 716.

Figure 8:
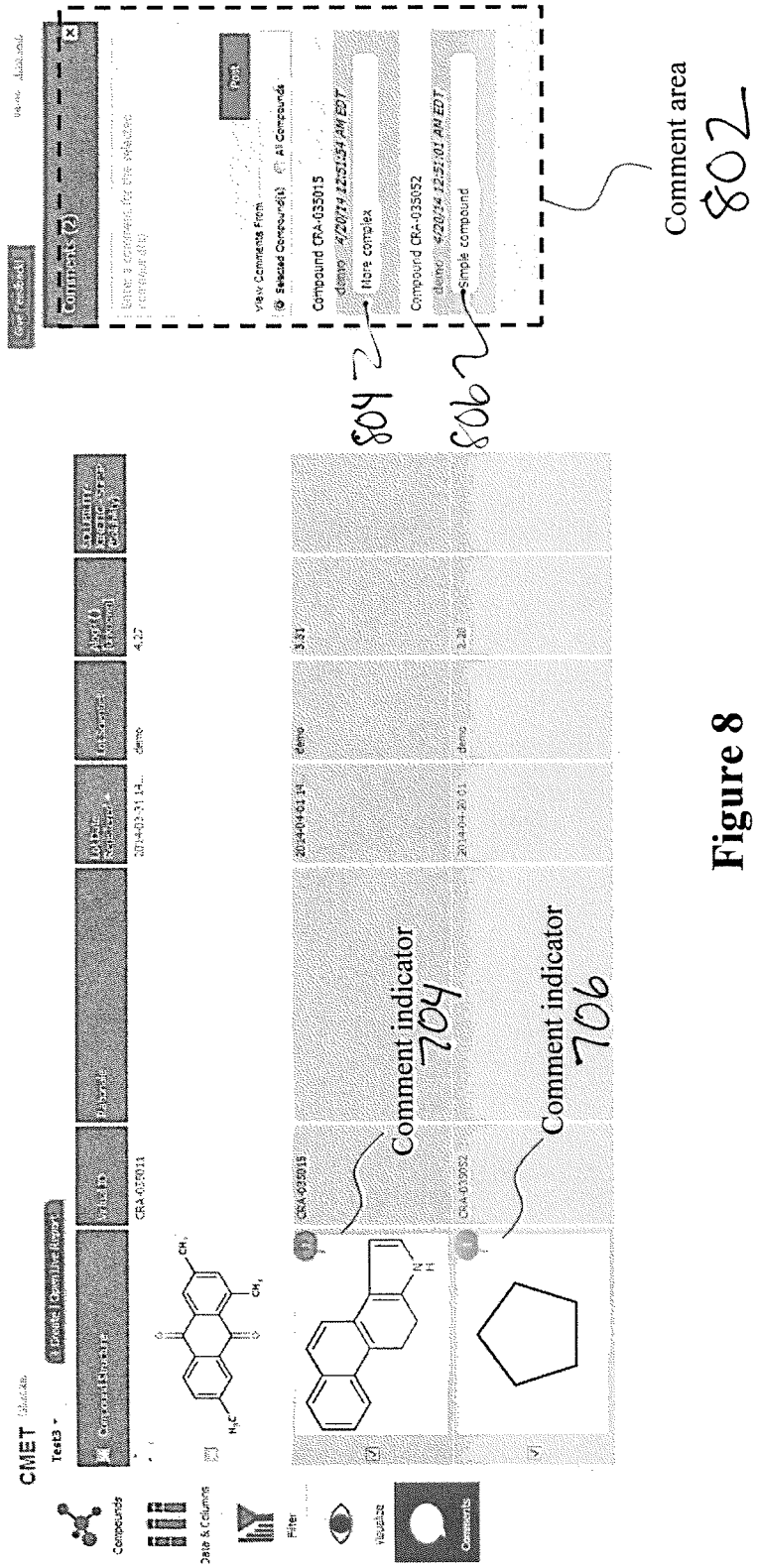

When the "Comments" tool is selected (shown in FIG. 8), the application displays a comment area 802 which can show the existing comments (804, 806) to the compounds in the Live Report, as well as allow a user to enter comments (e.g., by typing, speaking, or via any other human-machine interface for inputting data including text, audio, and other data) on a selected compound or all compounds. As shown in FIGS. 7 and 8, comment indicators (e.g., balloons) 704, 706, indicate the existence of one or more comments for the associated row/compound. Although shown as part of the structure column, the indicators could appear elsewhere and take on a different form. Comments can be considered conversations among the users about compounds. While the comments are shown in an area outside of the grid view of the Live Report, they can also be considered part of the Live Report content. Comments on a compound created in one Live Report may also be automatically retrieved and displayed in another Live Report containing the same compound, as the database may store each comment and associate it with the relevant compound(s). This allows users to see previous conversations that may have been had about a compound. The Live Report interface can be configured such that after the comments are entered, the cells in the Live Reports that present the compound structures can be automatically updated to include an indicator showing the presence of comments. Clicking the balloon can display the comment area if it is not already displayed.

The web user interface can also include an application module (e.g., a JAVA applet, WebGL, ActiveX control, an embedded Flash application, or another browser plug-in) to present a three-dimensional view of any selected compound in the Live Report, and allow the user to pan, rotate, zoom in and out, and inspect the compound (molecule) in various rendering modes. The module can be activated by clicking on the "Visualize" tool in the tool box shown in any of the FIGS. 3-7 (interface not shown). In one embodiment, the server application is designed and configured to interact with a 3D visualizer, such as that offered by Schrödinger LLC under the tradename PyMOL. The server application receives user commands regarding the creation and manipulation of 3D models, and converts those controls into commands compatible with and able to be interpreted by the visualizer. In other words, the server application includes a set of controls which accesses functions available in the 3D visualizer and can set customized views on the displayed information. In the present embodiment, each user has its own view of the 3D model; however, in alternate embodiments the system (server side application) stores parameters defining a user's view at the server (database 104), which are then used to present that user's view when the same and other users run the Live Report and view the 3D model. In another embodiment, the client side applet or server side application causes parameters defining the user's last 3D view to be stored in the browser, at the user's computing device 106 (e.g., in a cookie), which can be retrieved whenever the user runs the Live Report so that user may return to the its last view. For example, when a user opens the 3D visualizer, the server side application first causes the user computing device to be checked for the cookie and, if present, examined for parameters setting the 3D view. If present, such parameters are utilized as part of the Live Report and the model is displayed in accordance with the parameters reflected in the cookie.

In the above discussions, the web interface on the user computing device is described from one user's view. Multiple users can simultaneously access a Live Report and modify the contents thereof by logging on the platform and entering the project space containing the Live Report. One user can also invite other users to join a collaborative session to share a Live Report by sending the URL of the Live Report to the users. A user who is not participating in an ongoing collaboration session may receive all or selected updates of the ideas being discussed in session. For example, the server application may be configured to detect, and generate a notice upon, the occurrence of one or more predefined criteria or events (e.g., addition of new compounds, addition of new experimental data), a newly proposed compound achieved a high computational score that exceeds a preset threshold, such that a non-participating user can receive a notification (e.g., an "in app notification" or an email based on the user email stored in the databases 104). Such notification can be triggered based on one or more criteria set by the user to receive the notification or another user (e.g., that created the Live Report to be shared). Such criteria may be stored in the database and associated with the user and/or the Live Report(s) to be shared.

When multiple authorized users are logged on to the same Live Report, any updates to the Live Report by any of the users (e.g., when a user uses his web interface to add new compounds, data, or comments, or otherwise make a modification of the Live Report definition), will be transmitted to the server, and saved in a server memory, a permanent storage device of the server, and/or into the server database.

Conflicts may arise when the multiple users attempt to make concurrent edits on a Live Report being shared in a collaborative session. Different approaches can be used to resolve or avoid such conflicts. For example, a Live Report stored on the server can be associated with a timestamp attribute "last_saved_date" which is updated whenever the Live Report is changed. In other words, in the present embodiment, there is no need for a user to separately "save" a Live Report, as the last version is automatically persisted and available for later access. When a user's browser retrieves the Live Report, the browser also retrieves the value of this attribute. After an item of the Live Report is edited by the user, the browser sends the updated attribute value to the server, along with the attribute value originally retrieved from the server. The server compares this updated value with the current value of the attribute stored on the server to determine whether there has been another update made since the last_saved_date timestamp value originally sent to the user (i.e., determining whether the Live Report was already updated by another user). If no other updates have been made, the update received from the user browser is permitted, and the value of the last_save_date attribute stored on the server is also changed to the new timestamp value. If another update has been made (e.g., by another user from a different browser), as indicated by the attribute value originally retrieved not equaling the value save in the database or the time of the edit is received, the most recent update can be considered invalid and the user can be presented with an error message. In essence, the user's change would have been to an out-dated version of the Live Report. Alternatively, the system can be configured such that whenever a first user attempts to edit an item of the Live Report in his view, such an item is locked for all other users (i.e., other users cannot make concurrent edits on the same item on the Live Report) until the first user completes his edit. Such "locking" of a Live Report could be accomplished. For example, by setting a flag in the database each time a user opens a Live Report, and removing the flag when the user exits the Live Report or otherwise relinquishes editorial control of it (e.g., in response to receiving a request from another user) by, for example activating an on-screen button.

The updates by one user received by the server, after being validated by the server, can be sent to other users' web interface so that all users can get near real-time updates of the Live Report. Each user's view of the Live Report can be automatically refreshed without the users having to manually re-open, refresh, or otherwise re-execute queries. For a user's edit on the Live Report that may require substantial time to complete on the server side, (e.g., a computational task or a complex database inquiry), any subsequent requests for such computational task by other users can be suppressed (and the users making the subsequent requests can be notified). After the server completes the task, the result is sent back to the requesting user's web interface as well as being loaded to the server database (or server memory). Then the result may be shared among other users through the refresh mechanisms discussed below.

Refreshing the Live Report for the multiple users in a collaborative session can be done based on a recurring time interval for each user (i.e., each user browser, via embedded code sent from the server when the user first logs in the collaborative session, can poll the server according to a time schedule to see if any updates have been made in the last time interval, and fetch such updates from the server). The server application can, in addition or alternatively, be configured to automatically push any updates received from one user to other users viewing the Live Report. Other schemes of refreshing, such as those that take into account the user activity, can also be used. For example, a user browser can, based on predetermined time intervals, check the time since any results in the Live Report were last fetched or sent from the server and the time since any user viewing the Live Report (as reflected in the database 104) was last active on the webpage (e.g., determined by an application module, script, etc. on the user device 106 detecting and transmitting an indicator of any of a number of webpage events that indicate user interaction, such as keypress, mouse movement, scrolling, etc.). These indications of users' interactions can be used to determine if the user's Live Report should be refreshed for that user and, if so, when. Alternatively, a timeout mechanism can be used. For example, whenever the Live Report is updated, the browser with the Live Report opened checks to see if the report is active for that user (e.g., by checking the user's interaction history with the webpage), which may be stored locally within a predetermined or dynamically determined "timeout period." If the user was active after the timeout period elapses, the user's Live Report is refreshed. If the user was not active, the report does not refresh. This allows for performance gains for the system as it need not be refreshing Live Reports that are not being looked at by a user. Also, if desired, refresh of a Live Report of a user can also be done by including a functional element in the user interface (not shown) that can be manually activated (e.g., clicked by the user) to request a refresh of the Live Report data from the server. In an alternate embodiment, updates to a Live Report are stored in a cache (memory) and if another user runs the Live Report, then the system accesses the cache to generate the Live Report instead of having the server application regenerate the Live Report.

The refresh of the Live Report on user browsers may be done in a way which does not overload the server 102. Thus, refreshing Live Reports with a large amount of data or that require heavy computation may be done less frequently. For example, the refresh rate of the Live Report on the user browsers can also be reduced based on user activity. For example, if a user has not actively interacted with or has navigated away from the web page containing the Live Report, the refresh rate can be reduced or suspended.

While all the changes made in one user's Live Report will be transmitted to the server, a user can configure his own interface to selectively display only those data that he/she wishes to see. For example, the interface can present a user with the ability to select hide or display the comment area, hide or display a given column, apply his own filter to display only a subset of the rows of the Live Report, etc. Each user may also set up their own preferences such that he or she will be presented an interface to their liking when they first log onto any or specified Live Reports. Each user may have a customized view for each or a group of Live Reports. Alternatively, customization of at least some elements of the Live Report view (e.g., coloring schemes, filters, sorting rules) can be suppressed and each user is presented with an identical view of the Live Report with respect to those elements that are designed to be uniform among all users.

While the data in the Live Report may be shared among all users in a collaborative session, the input interface for each user may be kept individualized. For example, when a user is drawing a molecule on the sketcher, the drawing process may be not shared with another user, and only the compound completed by the sketcher and entered into the Live Report is shared among the users. Each user may be given the ability to control which of their own ideas to "publish" to other members of the team. For example, a user may sketch a compound of his or her interest, and compute a certain property of the compound to see the preliminary result, and then he or she can decide whether to release the idea to other users. This may be accomplished by using a "preview properties" feature, which allows for quick running computations to be calculated on the fly without adding the molecule/compound to the Live Report. Once it is added to the Live Report, it becomes accessible to anyone with access to that Live Report.

In certain embodiments a user is provided the ability to designate a Live Report or any row (compound) or column (data) that the user adds as "private," namely viewable and usable only by that user. Such information is flagged in the databases and, when the Live Report is run for another user, is excluded from the Live Report. In still other embodiments, a user may designate data added by the user as "unpublished," namely available for other users to see in the particular Live Report in which the user added it, but not available to use in other Live Reports.

Some collaborative team members (users) may be unable to attend a scheduled collaborative session. Also, certain data may be unavailable in a collaborative session but become available later. The server side application can be configured to generate alerts or more detailed reports/summaries to send to all or selected collaborative team members when new data or structures of interest are available (either created by the members of the collaborative team, or provided in external database or source, e.g., when a new experimental result for a previously discussed compound become available from a new scientific publication).

Figure 9:
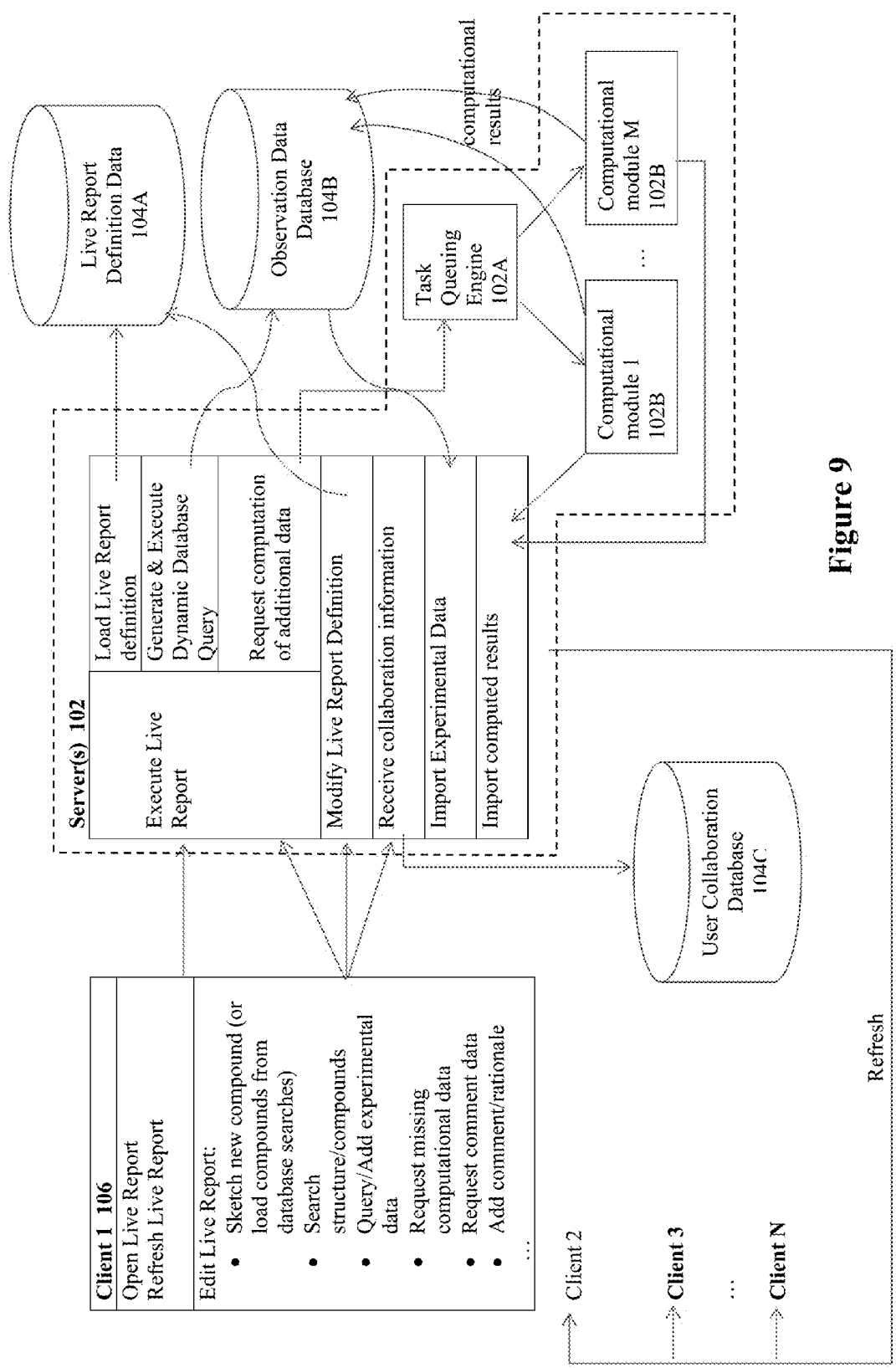
FIG. 9 is an information flow diagram illustrating components, processes and information flow according to one embodiment of the present invention.

FIG. 9 is an information flow diagram, depicting components and functions of a system according to certain embodiments of the present invention, such as that of FIGS. 1-8. Each user of a collaborative team uses a web computing application on a user computing device 106 (a "client") to access the server 102 and participate in a collaborative session. For brevity, only representative functions performed on a client (client 1) are shown in FIG. 9. Similarly, only some of the operations performed by the server 102 in response to the requests by client 1 are summarized in FIG. 9 (enclosed by the area defined by the dashed line), with discrete operations shown in different boxes for purpose of clarity. When a user first logs on the server 102 and opens a Live Report on his web application, a request is sent to the server 102 to "execute" the Live Report requested, which includes: loading the Live Report definition from a Live Report definition database 104A, executing database query for observation data (including experimental data) on an observation data database 104B; and requesting computation of data for the compounds based on computational models when those data are not already available in the observation data database.

In general, the Live Report definition database of the present embodiment stores three types of data, including: meta data for each Live Report, such as the name, template, color rules and the like; definition of each row or compound included in the Live Report and definition of each column or data included.

Although only one observation data database 104B is shown in FIG. 9, multiple observation databases can be used, each having different tables or database schemas. The computational tasks can be first processed by a task queuing engine 102A to assign one or more computational modules 102B for the tasks as well as determine the order in which the tasks are to be performed. The tasks are then performed by the computational modules 102B, with the computational results included in a server memory as well as in the observation data database 104B. Each client also requests comment data for compounds visible in the Live Report. When any user enters comment data, the server 102 can save the comment data on the memory of the server and/or the coupled database(s) 104.

A Live Report definition can be modified by a user, e.g., by requesting a computational task to be performed by the server 102, or requesting a query to be run by the server 102 to retrieve an experimental data associated with the compound (or by renaming the title of a column, changing sort order of the data in certain columns, if such actions are included in the Live Report definition). The Live Report viewed on the client device 106 which initiates the changes can be immediately updated (e.g., a new column is immediately added on the grid view of client 1's Live Report, with a status identifier indicating the data being computed by the server 102, which is replaced by the computed data when the computation is completed). The Live Report shown other clients (e.g., client 2, 3 . . . N) will be refreshed according to the schemes discussed herein.

The observation data database 104B can store observation data (e.g., experimental data or computed data associated with synthesized or putative compounds, metadata regarding the observations (e.g., data specific to a pose of a ligand and target, value for a certain experimental assay, how the data is entered into the system)). The user collaboration database 104C can include the user comments or rationale provided for compounds. While the databases depicted in FIG. 9 are shown as separate databases, such a configuration is merely illustrative and not limiting. For example, a database can be used to store both observation data tables and collaboration data tables. Observation data can be aggregated from a same observation database or over multiple observation databases through a pivoting process to obtain aggregate properties for multiple values (e.g., average, geometric mean, minimum, maximum, etc.).

FIG. 10 depicts illustrative examples of certain data tables and their relationship in the observation data database(s) 104B according to some embodiments. The tables are connected by lines indicating relationship between the tables. For example, the observation database(s) can include a compound table ("syn_compound_lot" table) which includes certain attributes of each compound in the database such as Sample ID ("sample_id"), ID of the salt form of the compound ("salt_id"), lot number ("lot_number"), project ID ("project_id"), source ID ("source_id"), ID of the document from which the compound is obtained ("document_id"), ID of the scientist proposing the compound ("person_id"), etc. Some of the attributes, e.g., "salt_id", "source_id" also serve as foreign keys to other tables, e.g., the "syn_salt" table and "syn_source" table. Likewise, the table storing the observation data (the "syn_observation" table) includes attributes reflecting experimental setup and results for each compound such as experimental result value ("Quantity"), experimental batch number ("primary-_groupno"), experimental concentration ("quantity_conc"), etc. Again, this table can be linked to other tables through shared keys.

For practical purposes, user collaboration database 104 can be separate from observation data database(s) 104B, and built for more direct access, better read and write performance, etc.

Upon the conclusion of the collaborative session, all the Live Reports created or updated during the sessions can be stored in server databases 104.

While illustrative embodiments of the invention have been disclosed herein, numerous modifications and other embodiments may be devised by those skilled in the art in accordance with the invention. For example, the various features described in the embodiments herein can be altered or combined, with fewer or greater features in any given embodiment and features from separate described embodiments combined into a single embodiment. Therefore, it will be understood that such modifications are within the spirit and scope of the present invention.

What is claimed is:

1. A computerized system for providing electronic collaborative drug discovery workplaces simultaneously accessible by multiple user computing devices, the system comprising:
   one or more electronic databases including a definition for each of multiple electronic workplaces, the definition including at least (i) information identifying the workplace; (ii) information identifying one or more compounds of interest; and (iii) information identifying data of interest for each compound, wherein the information identifying a compound of interest includes at least a compound structure data field indicative of a compound's chemical structure and a separate compound formula data field indicative of a compound's chemical formula;
   at least one server computer operable in accordance with computer programming to:
   establish a connection with a first user computing device;
   in response to a request from the first user computing device, execute a requested workplace based on a corresponding workplace definition, wherein compounds are added to the workplace using a sketcher that allows users to draw a compound's chemical structure, and wherein executing the workplace includes:
   access the database and the definition for the requested workplace, and
   cause display on the first user computing device of the certain workplace, the display including a graphical representation of compounds that were not filtered based on the compound structure data fields and compound formula data fields for the displayed compounds.

2. The system of claim 1 wherein the server computer is further operable to:
   receive from the first user computing device an indication of a new compound for
   inclusion in the requested workplace, the new compound not previously included in the database;
   update the database to include the new compound, including a compound structure data field for the new compound and a compound formula data field for the new compound;
   providing an indication of the new compound to a second user computing device; and
   in response to a request from the second user computing device, adding the new compound to another workplace.

3. The system of claim 1 wherein the server computer is further operable to:
- establish a connection with a second user computing device;
- in response to a request from the second user computing device, executing the requested workplace based on the corresponding workplace definition, wherein executing the workplace for the second user computing device occurs while the requested workplace is being displayed on the first user computing device;
- updating the requested workplace definition in response to receiving from the second user computing device an indication of an addition of an additional compound;
- causing the display on the first user computing device to include the additional compound;
- in response to a request from the first user computing device, applying a filter to the requested workplace; and
- causing the display on each of the first and second user computing devices to update based on the filter.

4. The system of claim 1 wherein the server computer is further operable to:
- receive from the user computing devices a first type of query of one or more of the databases in connection with a certain workplace, the first type of query being a onetime search to display results of the query without automatically permanently including the results of the query as part of the workplace; and
- receive from the user computing devices a second type of query, the second type of query being a persistent query and permanently including results of the query as part of the workplace.

5. The system of claim 4 wherein the first type of query is based on structure of compounds and the second type of query is based on structure and associated data stored in one or more of the databases.

6. A computerized method of drug discovery utilizing one or more servers in communication with one or more electronic databases and multiple user computing devices, the method comprising:
- creating a first electronic workplace in response to an input from a first user computing device;
- making the first workplace accessible to multiple user computing devices simultaneously, wherein compounds are added to the workplace using a sketcher that allows users to draw a compound's chemical structure;
- adding one or more compounds to the first workplace in response to an input from a first or second user computing device, wherein the compounds are predefined in the databases;
- adding a new compound to the first workplace, the new compound not being predefined in the databases;
- updating the databases to reflect the new compound;
- generating computational data for the compounds and new compound in the first workplace and adding the computational data as part of the workplace;
- updating the databases to reflect the computational data for the new compound;
- creating a second electronic workplace in response to input from a second user computing device;
- adding the new compound and associated computational data to the second workplace in response to input from the second user computing device; and
- making the second workplace accessible by multiple user computing devices.

7. The method of claim 6 wherein updating the databases to include the new compound includes updating a compound structure data field for the new compound and a compound formula data field for the new compound.

8. The method of claim 6 further comprising:
- receiving a first type of query in connection with the first workplace from one of the user computing devices and in response causing results of the first query to be displayed to the one of the user computing devices; and
- receiving a second type of query in connection with the first workplace from one of the user computing devices and in response causing the databases to be updated to associate results of the second query with the first workplace.

* * * * *